(12) United States Patent
Kellerman et al.

(10) Patent No.: US 6,866,642 B2
(45) Date of Patent: Mar. 15, 2005

(54) ENHANCED METHOD FOR JOINING TWO CORE WIRES

(75) Inventors: Brad Kellerman, Escondido, CA (US); Marc L. Speck, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 145 days.

(21) Appl. No.: 10/303,396

(22) Filed: Nov. 25, 2002

(65) Prior Publication Data

US 2004/0102720 A1 May 27, 2004

(51) Int. Cl.$^7$ .................................................. A61B 5/00
(52) U.S. Cl. ........................................................ 600/585
(58) Field of Search .............................. 600/585, 433–435; 604/523–525, 533

(56) References Cited

U.S. PATENT DOCUMENTS

| | | | |
|---|---|---|---|
| 4,827,941 A | | 5/1989 | Taylor et al. |
| 4,875,489 A | | 10/1989 | Messner et al. |
| 4,966,163 A | | 10/1990 | Kraus et al. |
| 5,109,867 A | * | 5/1992 | Twyford, Jr. ............... 600/585 |
| 5,415,178 A | | 5/1995 | Hsi et al. |
| 5,513,650 A | * | 5/1996 | Johansen ..................... 600/508 |
| 5,637,089 A | | 6/1997 | Abrams et al. |
| 5,853,375 A | * | 12/1998 | Orr ............................. 600/585 |
| 5,951,494 A | | 9/1999 | Wang et al. |
| 6,001,068 A | * | 12/1999 | Uchino et al. .............. 600/585 |
| 6,165,292 A | | 12/2000 | Abrams et al. |
| 6,248,082 B1 | | 6/2001 | Jafari |
| 6,280,539 B1 | | 8/2001 | Abrams et al. |
| 6,451,026 B1 | * | 9/2002 | Biagtan et al. ............. 606/108 |
| 6,544,197 B2 | * | 4/2003 | DeMello ..................... 600/585 |
| 2002/0049392 A1 | | 4/2002 | DeMello |
| 2003/0069521 A1 | * | 4/2003 | Reynolds et al. ........... 600/585 |

FOREIGN PATENT DOCUMENTS

| | | |
|---|---|---|
| EP | 0 806 220 A2 | 11/1997 |
| EP | 0 838 230 A2 | 4/1998 |
| WO | WO 03/30982 A2 | 4/2003 |

OTHER PUBLICATIONS

Internet Web Site—www.microlumen.com/polymide.htm (MicroLumen); Products, 2 pgs., visited Oct. 4, 2002.
Jafari et al.: "Apparatus and method for joining two guide wire core materials without a hypotube" U.S. Appl. No. 10/032,873, filed Nov. 25, 2002.
Pacetti.: "MRI compatible guide wire", U.S. Appl. No. 10/034,715, filed Dec. 25, 2001.

\* cited by examiner

*Primary Examiner*—Charles Marmor
(74) *Attorney, Agent, or Firm*—Fulwider Patton Lee & Utecht, LLP

(57) ABSTRACT

An intravascular guide wire having at least two core materials joined together. There is a wire core having a proximal core section with a proximal end and a distal end and a distal core section with a proximal end and a distal end. The distal end of the proximal core section and the proximal end of the distal core section are formed into complementary shapes, and then placed into a flexible sleeve in opposing directions. Inside the flexible sleeve, the complementary shaped ends are joined together through bonding, welding, brazing, cementing, or soldering. The flexible sleeve can be either a stretched coil or a polyimide sleeve, each with an outer diameter similar to the outer diameter of the core wire, therefore the guide wire does not require additional grinding to reduce the outer diameter of the joined section.

19 Claims, 2 Drawing Sheets

ENHANCED METHOD FOR JOINING TWO CORE WIRES

BACKGROUND OF THE INVENTION

This invention relates to the field of medical devices, and more particularly to a guide wire for advancing a catheter within a body lumen in a procedure such as percutaneous transluminal coronary angioplasty (PTCA).

In a typical PTCA procedure, a guiding catheter having a pre-formed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guide wire is first advanced by itself through the guiding catheter until the distal tip of the guide wire extends beyond the arterial location where the procedure is to be performed. Then a catheter is mounted onto the proximal portion of the guide wire which extends out of the proximal end of the guiding catheter which is outside of the patient. The catheter is advanced over the guide wire, while the position of the guide wire is fixed, until the operative element on the catheter is disposed within the arterial location where the procedure is to be performed. After the procedure is performed, the catheter may be withdrawn from the patient over the guide wire or the guide wire repositioned within the coronary anatomy for an additional procedure.

Conventional guide wires for angioplasty, stent delivery, atherectomy and other intravascular procedures usually have an elongate core member with one or more segments near the distal end thereof which taper distally to smaller cross sections. A flexible body member, such as a helical coil or a tubular body of polymeric material, is typically disposed about and secured to at least part of the distal portion of the core member. A shaping member, which may be the distal extremity of the core member or a separate shaping ribbon which is secured to the distal extremity of the core member, extends through the flexible body and is secured to the distal end of the flexible body by soldering, brazing or welding; or an adhesive may be used in the case of polymeric flexible bodies which forms a rounded distal tip. The leading tip is highly flexible and will not damage or perforate the vessel. The portion behind the distal tip is increasingly stiff, which better supports a balloon catheter or similar device.

A major requirement for guide wires is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guide wires to make them more suitable for their intended uses, but these two properties are for the most part diametrically opposed to one another in that an increase in one usually involves a decrease in the other.

In order to fulfill these requirements, guide wires now include two different types of material joined together with a connecting tube so that a proximal core will consist of a material having sufficient column strength and a distal core will be made of a flexible material to advance through a body lumen. Currently, an expensive nitinol hypotube or connecting tube is used to join a proximal stainless steel core to a nitinol distal core on certain types of guide wires. An example of this type of guide wire can be seen in, for example, U.S. Pat. No. 6,248,082 (Jafari).

SUMMARY OF THE INVENTION

The present invention is directed to an intravascular guide wire having at least two core materials joined together without the use of a nitinol hypotube. An earlier filed application, U.S. Ser. No. 10/032,873 ('873 application), filed on Dec. 27, 2001, now issued on Mar. 9, 2004 as U.S. Pat. No. 6,702,762 (Jafari et al.), titled "Apparatus And Method For Joining Two Guide Wire Core Materials Without A Hypotube" describes the use of several complementary shaped joints used to replace the use of a hypotube. This patent is herein incorporated by reference in its entirety.

In one embodiment, the invention provides a core having a proximal core section with a proximal end and a distal end and a distal core section with a proximal end and a distal end. It is preferred that the proximal core section is made of stainless steel to provide sufficient column strength, and the distal core section is made of nitinol which is flexible to advance through a tortuous body lumen. The distal end of the proximal core section and the proximal end of the distal core section are plunge ground to a smaller diameter, and then the ends are tapered. It is possible, however, to form the distal end of the proximal core section and the proximal end of the distal core section into any complementary shape, such as those disclosed in the '873 application. The ends are then placed into a sleeve in opposing directions such that the two tapered surfaces face each other and the ends overlap one another. The sleeve may be either a spring coil, a polymeric sleeve, such as a polyimide sleeve or tube, a patterned tube, or other flexible polymer or metallic material that can accommodate the two ends. The sleeve material has essentially little or no stiffness, especially when compared to a nitinol hypotube. A mass of hardened material, such as solder or glue, is used to join the assembly together. Once bonded, the outer diameter of the sleeve is the same as or similar to that of the core wire, thereby eliminating the need for post-bonding procedures, such as grinding to achieve a desired outer diameter.

The mass of material that is used to join the proximal and distal cores may be any bonding material, including the following: solder, brazes, adhesives, epoxies, glues, laser welds, spot welds, etc. that are preferable for the wire type and provide the required functional attributes. In one embodiment where the sleeve is a spaced coil, joining the two cores together can be accomplished by dispensing, for example, solder in-between the connecting ends and filling in the spaces in the coil. In another embodiments, where the sleeve is a polymeric sleeve, the cores can be joined together by filling the polymeric sleeve with an adhesive so that the ends are secured together when they are placed inside the sleeve. Any excess adhesive that flows outside of the polymeric sleeve or patterned tube is simply removed. An additional embodiment may include a patterned tube made of stainless steel or a superelastic material with a pattern cut into the tube, much like a stent to provide flexibility. Depending on the pattern cut into the tube, the two cores of the guide wire may be joined inside the patterned tube using methods similar to those described with the use of a coil or polymer sleeve.

The present invention method of joining a proximal and a distal core section can be applied to any two wires, and to any guide wire having a diameter ranging from about 0.006 inch to about 0.040 inch (0.015 cm–0.10 cm). Wire materials that may be combined through this method include, but are not limited to, all types of metals, alloys, polymers, and composite materials.

The present invention can also be used to create a guide wire with two lap joints. One joint would connect the proximal core section to the distal core section, and the second joint would connect a shaping ribbon to the distal end of the distal core section.

These and other advantages of the invention will become more apparent from the following detailed description thereof and the accompanying exemplary drawings.

DETAILED DESCRIPTION OF THE PREFERRED EMBODIMENTS

Figure 1:
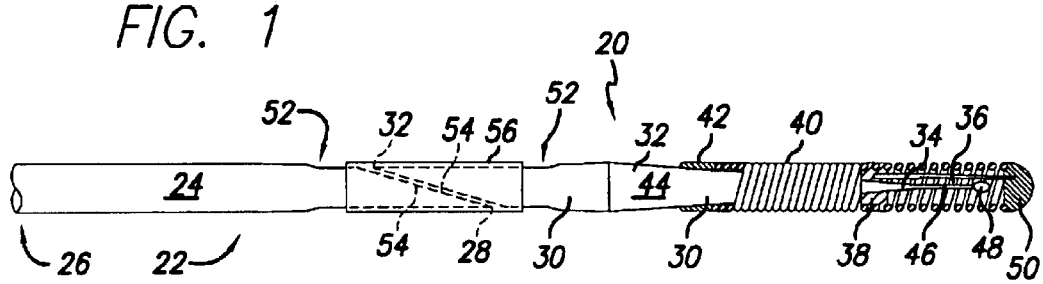
FIG. 1 is a side elevational view showing one embodiment of the present invention guide wire with two sections joined together.

The present invention is directed to a guide wire that uses at least two core materials that are joined at an interface. FIG. 1 illustrates in a side elevational view one embodiment of the present invention guide wire, generally designated 20, that is adapted for insertion into a patient's body lumen, such as an artery or vein. In this embodiment, the intravascular guide wire 20 has at least two core materials joined or secured together. In particular, the guide wire 20 has a core 22 with a proximal core section 24 having a proximal end 26 and a distal end 28, and a distal core section 30 having a proximal end 32 and a distal end 34. It is preferred that the proximal core section 24 is made of stainless steel, and the distal core section 30 is made of nitinol. However, the core sections may be made out of any material known in the guide wire art.

In the embodiment as shown in FIG. 1, the guide wire 20 also includes a shapeable member 36 which can be secured to the distal core section 30 by a solder or weld bead 38, and a flexible body 40 such as a helical coil. Preferably, the flexible body 40 is disposed about and secured to the distal core section 30 by a solder or weld bead 42. The distal core section 30 has an optional tapered core segment 44 and an optional flexible core segment 46 which is distally contiguous to the tapered core segment. At the very distal end of the flexible core segment 46 is a rounded distal extremity 48. Of course, the rounded distal extremity 48 may be of other shapes and sizes, can be flattened, or omitted altogether. In fact, in an alternative embodiment core-to-tip design, the flexible core segment 46 extends continuously to engage a rounded tip 50 at the very distal end of the guide wire 20.

In one embodiment, the distal end 28 of the proximal core section 24 and the proximal end 32 of the distal core section 30, now referred to as the connecting ends 28 and 32, overlap one another inside a flexible sleeve. Before the joint is formed, both of the connecting ends are first plunge ground to a smaller diameter. This initial plunge grind reduces the outer diameter of the connecting ends by about 0.001 inch (0.0254 mm) to about 0.003 inch (0.762 mm). It is preferred that the reduction in diameter be minimized, because the removal of additional material adversely impacts the local bending properties and impairs the tensile strength of the core wire. A plunge grind section 52 is best shown in FIG. 2.

In other embodiments, the proximal core section 24 and the distal core section 30 may have differing outer diameters, in which case the initial plunge grind will be different on each of the connecting ends 28 and 32. For example, if the outer diameter of the distal core section is about 0.0098 inch, and the proximal core section has an outer diameter of about 0.0132 inch, then only the proximal core section will be plunge ground to reduce its outer diameter to be substantially equal to the outer diameter of the distal core section. As this example shows, the initial plunge grind may only be performed on one of the connecting ends 28 and 32.

Figure 2:
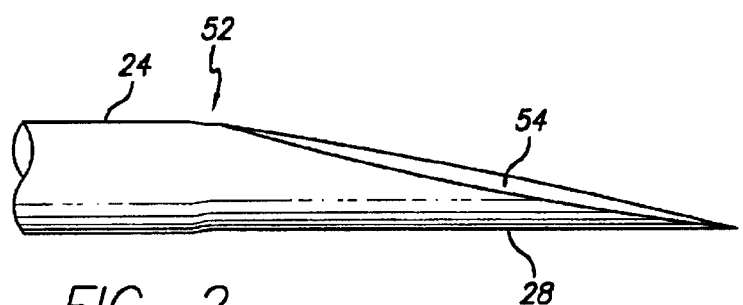
FIG. 2 is a perspective view of the tapered distal end of the proximal core section.
Figure 2A:
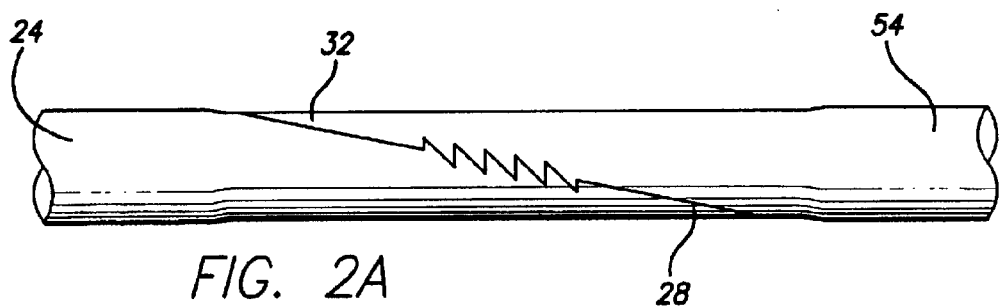
FIG. 2A is a perspective view of the tapered distal end of the proximal core section and complementary shaped proximal end of the distal core section, with serrations formed in each end to help lock the two ends together.

Still referring to FIG. 2, a taper or bevel 54 is also formed on the connecting ends 28 and 32. The taper 54 is formed on one side of the ground sections 52 of the connecting ends 28, 32 by surface grinding, milling, electrical discharge machining (EDM), laser cutting, or any other appropriate process known in the art. The length of the taper or bevel 54 can be between about 1 mm and about 5 cm, and is preferably about 0.80 cm to about 1.5 cm for a 0.014 inch outer diameter core wire. Naturally, the length of the tapered or beveled section 54 influences the amount of interfacing surface area available to be welded, bonded, soldered, etc. Another factor that influences the amount of interfacing surface area is the final outer diameter of the connecting ends 28 and 32 after the initial grind. It has been contemplated that any other complementary shapes can be formed into the connecting ends, and also serrations (FIG. 2A) can be added to help lock the two ends together. If desired, the tapered area can be gold tinned or etched for improved solderbility.

The connecting ends 28 and 32 are then inserted into a flexible sleeve 56 from opposing directions such that the two tapered surfaces face each other and overlap one another. The large overlap of the connecting ends 28 and 32 ensures efficient torque transmission, smooth bending properties, and sufficient tensile strength from the proximal core section 24 to the distal core section 30. Once the ends are positioned inside the flexible sleeve 56, the assembly may then be secured together using an anaerobic adhesive or solder, or any other bonding material that meets design and strength requirements, such as epoxies, glues, adhesive, laser welding, and spot welding. In an embodiment where solder is used to form a joint between the connecting ends 28 and 32, it is preferred that the solder include SnAg 95-5 along with NiTi flux 400. However, any type of compatible solder having the proper strength to bond core materials together could be used, such as other ratios of silver-tin solder, including 90-10, and also gold-tin solder may be used. In an embodiment where an adhesive is used, it is preferred that the adhesive be an anerobic adhesive.

One advantage of using a flexible sleeve is that is serves as the fixturing for assembling the joint, which makes the manufacturing process easier. Another advantage of using the flexible sleeve 56 is that improves joint strength and eliminates a potential for the ends to "peel" apart during a tight bend.

The dimensions of the flexible sleeve 56 and plunge ground connecting ends 28 and 32 are such that the outer diameter at the joint around the flexible sleeve is the same as or similar to that of the original core wire 22. Therefore, post bonding procedures, such as grinding or re-rounding operation, normally used to achieve the desired outer diameter are not needed. The flexible sleeve also provides a smooth transition with a generally constant diameter from the proximal core section to the distal core section.

Figure 3:
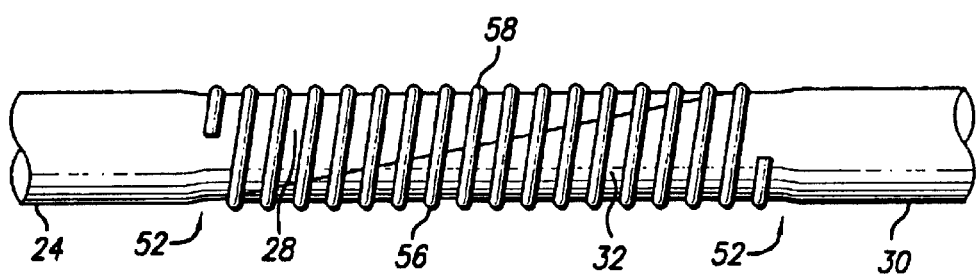
FIG. 3 is a side elevational view of one embodiment of the present invention where the tapered distal end of the proximal core section and the tapered proximal end of the distal core section are facing one another inside a spaced coil.
Figure 4:
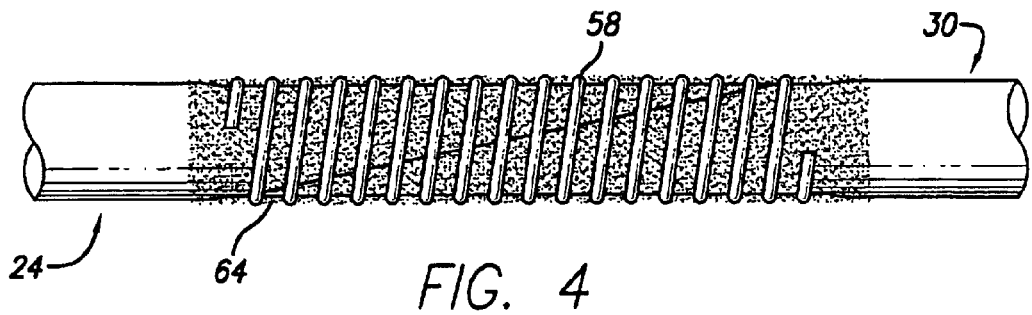
FIG. 4 is a side elevational view of the embodiment shown in FIG. 3 with solder connecting the assembly together.

One embodiment shown in FIG. 3, uses a coil or spring 58 as the flexible sleeve 56. It is preferred that the coil 58 has individual coils that are spaced apart or stretched. As described above, the connecting ends 28 and 32 are inserted into the coil 58 from opposing ends with the tapered surfaces 54 facing and overlapping each other. The assembly can then be secured together using a hardening material such as solder. As shown in FIG. 4, the assembly including the coil 58 has been soldered using techniques known in the art, with the solder, designated 64, filling the gap in-between the connecting ends 28 and 32 and the spaces between individual coils. When using a coil or spring, the soldering process is easier because the solder wicks down into the coils similar to a center solder.

The flexible sleeve 56, or in this embodiment the coil 58, is sized depending on the amount of material removed from the outer diameter at the distal end 28 of the proximal core section 24 and the proximal end 32 of the distal core section 30. The coil 58 should be sized so that when positioned over the connecting ends 28 and 32, the outer diameter around the soldered coil is the same as or similar to the original outer diameter of the core wire 22. In one embodiment, the diameter of the connecting ends 28 and 32 is reduced by 0.0015 inch (0.038 mm), and a 0.001 inch (0.025 mm) coil is used to jacket or sleeve the joint, after which solder is used to bond the three components together. In other embodiments, the diameter of the connecting ends can be reduced by about 0.001 inch to about 0.003 inch, and the size of the coil will vary depending on the amount of material removed from the core wire. If a greater amount of material is removed from the outer diameter of the connecting ends 28 and 32, the bending properties will be adversely impacted and the tensile strength of the core wire will be impaired. On the other hand, if less material is removed from the outer diameter of the connecting ends 28 and 32, a smaller coil will have to be used which creates handling difficulties because of the fragile nature of the smaller coil. This embodiment describes the use of a separate coil to cover the joint, however, it is possible to extend the intermediate coil to cover the joint, thereby minimizing the number of parts needed to manufacture a guide wire.

Figure 5:
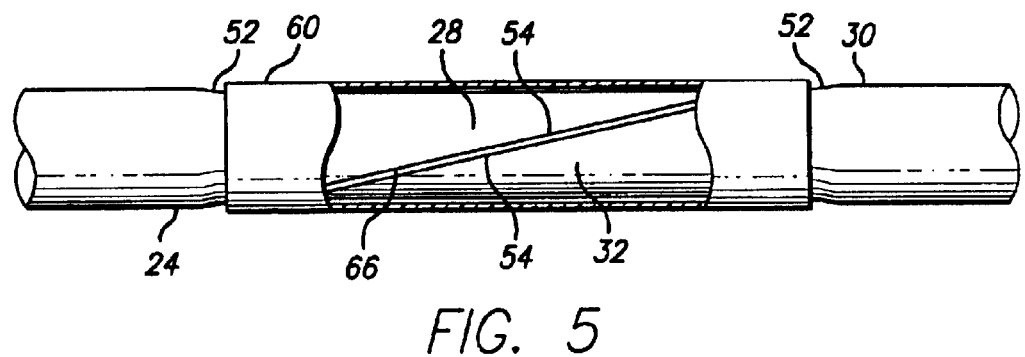
FIG. 5 is a partial cross-sectional view of another embodiment of the present invention where the tapered distal end of the proximal core section and the tapered proximal end of the distal core section are joined together inside a polyimide sleeve.

In another embodiment shown in FIG. 5, the flexible sleeve 56 is a polymeric sleeve 60. It is preferred that the polymeric sleeve is actually a polyimide sleeve or tube because of its strength, flexibility, kink resistance, high modulus, and availability with relatively thin walls. However, other polymers may be used for sleeve such as polyurethane, polyethylene, polytetrafluoroethylene (PTFE), polyester, and others. When using the polyimide sleeve 60 with the present invention an adhesive, generally designated 66, is inserted into the polyimide sleeve to join the connecting ends 28 and 32 together. In this regard, the polyimide sleeve 60 acts like fixture for securing the two sections of wire together. A variety of adhesives may be used inside the polyimide sleeve, such as a cyanoacrylate adhesive, UV cure adhesive, anaerobic adhesive, or an epoxy. The connecting ends 28 and 32 are inserted into the polyimide sleeve 60 from opposing ends so the taper 54 on each end faces and overlaps one another. When the connecting ends 28 and 32 are inserted into the polyimide sleeve 60, the adhesive is forced to cover and secure the tapered connecting ends. Any extra adhesive inside the polyimide sleeve 60 will flow out of the sleeve where it can be removed.

When using a polyimide sleeve 60, less material needs to be removed from the connecting ends 28 and 32 because the polyimide sleeve can be manufactured with a wall thickness of about 0.0004 inch (0.01 mm). The wall thickness of the polyimide sleeve is actually about 3.75 times thinner than the previously used nitinol hypotube which has a wall thickness of about 0.0015 inch (0.038 mm). Although the outer diameter of the connecting ends 28 and 32 can be reduced from about 0.001 inch to about 0.003 inch, it is preferred that the outer diameter of the connecting ends be reduced by about 0.001 inch when using the polyimide sleeve 60 having an outer diameter the same as or similar to the original outer diameter of the core wire 22.

There is no need for a post assembly grinding or re-rounding operation with this design because the outer diameter of the polyimide sleeve is the same as or similar to that of the original core wire. The polyimide sleeve 60 gives little or no support to the assembled guide wire 20, whereas the previously used nitinol hypotube supported nearly all the bend and tensile load at the joint between the proximal core section and distal core section. Since the polyimide sleeve 60 provides relatively no stiffness to the guide wire 20, the joint between the proximal and distal core sections and the core wire supports most of the bend and tensile load of the core wire. Therefore, an advantage of the polyimide sleeve 60 is that is provides a smooth bending profile. The use of the polyimide sleeve also eliminates a potential for the connecting ends to "peel" apart during a tight bend. In an assembled guide wire, the joint between the proximal core section 24 and the distal core section 30 is virtually undetectable by the human eye, and the polyimide sleeve provides a smooth constant transition with a generally constant diameter from the proximal core section 24 to the distal core section 30.

Figure 6:
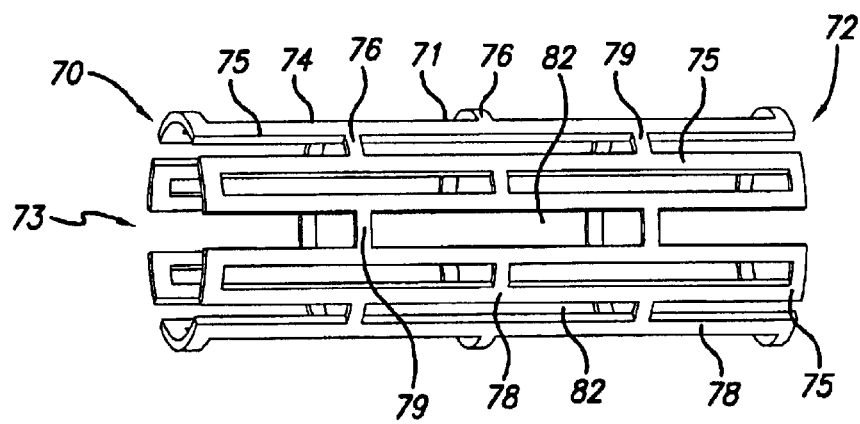
FIG. 6 is a perspective view of another embodiment of a sleeve which is a patterned tube.

Another type of sleeve that can be used to secure the connecting ends 28 and 32 together is a patterned tube 70, which is shown in FIG. 6. The figure represents one example of a tube having a pattern cut into it to increase flexibility. Referring to FIG. 6, the patterned tube 70 has a tubular shaped member 71 having a proximal end 72 and a distal end 73, with a plurality of elongate members 75 and 76 forming a wall surface 74. In this embodiment, the elongate members 75 and 76 are a plurality of thin bars 78, 79. The thin bars 78 and 79 are preferably fixedly secured to one another where the bars intersect with one another. Bars 78, 79 preferably have a thin, rectangular cross-sectional configuration, and may be joined to one another in any conventional manner, such as by welding, brazing, soldering, or may be formed integral with one another. Preferably, tubular shaped member 71 is initially a thin-walled stainless steel tube or a superelastic tube formed of nitinol, and the openings 82 between the intersecting bars 78 and 79 are formed by a conventional etching process, such as electromechanical or laser etching, whereby the resultant structure is a tubular shaped member 71 having a plurality of intersecting elongate members 78, 79. In a preferred embodiment, exemplified in FIG. 6, the openings 82 between the intersecting bars 78 and 79 introduce a plurality of discontinuities into the circumference of each of the proximal end 72 and the distal end 73. It should be understood that the embodiment of the patterned tube 70 could also be generally described as a wire mesh tube. The patterned tube 70 could also have a pattern with rings and links (both linear and non-linear) such as a stent pattern which are known in the art. However, unlike a stent design, the patterned tube 70 would have a limited circumferential expandability. The patterned tube 70 should have non stretchable struts circumferentially, and longitudinal struts that are stretchable to help provide a smooth bending profile.

Similar to the above embodiments, the connecting ends 28 and 32 are inserted into the patterned tube 70 from opposing ends so the taper 54 on each end faces and overlaps one another. Once the ends are positioned inside the patterned tube 70, the assembly may then be secured together using an anaerobic adhesive or solder, or any other bonding material that meets design and strength requirements, such as epoxies, glues, adhesive, laser welding, and spot welding. If the patterned tube 70 has relatively little surface area, then it would be preferred to wick solder into the gap in-between the connecting ends 28 and 32 and the spaces between individual struts.

The above embodiments describe the use of a coil, polymeric sleeve and a patterned tube, however, any type of sleeve, tubing or coating could be used to cover the joint in order to provide fixturing and alignment for the connecting ends, and prevent the connecting ends from "peeling" apart.

During initial tensile strength experiments comparing the use of a nitinol hypotube with the use of a flexible sleeve (coil and polyimide sleeve), the flexible sleeve out performed the nitinol hypotube. With a guide wire using a nitinol hypotube to join a proximal core section formed of stainless steel (SS) and a distal core section formed of nitinol (NiTi), the tensile strength ranged from 3.52–5.12 lbs. Comparatively, a guide wire using a 0.001 inch coil and solder to join a proximal core section formed of SS and a distal core section formed of NiTi, the tensile strength ranged from 14.91–17.04 lbs., over 3 times the tensile strength of the nitinol hypotube. A guide wire using a polyimide sleeve and an anerobic curing adhesive to join a proximal core section formed of SS and a distal core section formed of NiTi, the tensile strength ranged from 6.32–9.75 lbs.

There is no change to how a guide wire produced with the disclosed methods is used. The methods described produce a guide wire with at least two core sections which are joined together using a flexible sleeve. Also these methods may be used to join any two wires together, and may even be used to attach a shaping ribbon onto the distal end of the distal core section, producing a guide wire with two lap joints. This embodiment includes at least three core materials that are joined or bonded together in the same manner as previously described for a single lap joint of two core materials. One embodiment would include a first lap joint connecting together a stainless steel section with a nitinol section, and the second lap joint connecting the nitinol section with another stainless steel section that can then be formed to act as a shaping ribbon. After the two lap joints are formed, there would be no need for post-bonding procedures such as grinding or re-rounding operation because the outer diameter around the two lap joints would already be the appropriate dimensions. Further, any wire can be formed containing any number of core materials or any number of lap joints using this method.

While a particular form of the invention has been illustrated and described, it will also be apparent to those skilled in the art that various modifications can be made without departing from the spirit and scope of the invention. It should be clear that the types of material used in the core sections may vary. Also, the size and dimensions of the guide wire can vary in terms of outer diameter, ground diameter, length, and ground length. Accordingly, it is not intended that the invention be limited except by the appended claims.

What is claimed is:

1. An intravascular guide wire, comprising:
   a core having a proximal core section with proximal and distal ends and a distal core section with proximal and distal ends; and
   a flexible sleeve covering the distal end of the proximal core section and the proximal end of the distal core section, the sleeve having proximal and distal ends, each end of the sleeve circumferentially surrounding the core, the sleeve defining a plurality of openings such that each end of the sleeve has a plurality of circumferential discontinuities;
   wherein the distal end of the proximal core section and the proximal end of the distal core section overlap one another.

2. The guide wire of claim 1, further comprising a mass of hardened material at a joint connecting the distal end of the proximal core section to the proximal end of the distal core section.

3. The guide wire of claim 2, wherein the mass of hardened material is disposed between the distal end of the proximal core section and the proximal end of the distal core section and encases the ends within the flexible sleeve.

4. The guide wire of claim 2, wherein the mass of hardened material includes a bonding material selected from the group consisting of solders, brazes, adhesives, epoxies, glues, laser welds, and spot welds.

5. The guide wire of claim 1, wherein the flexible sleeve has an outer diameter that is generally equal to the outer diameter of the core.

6. The guide wire of claim 1, wherein at least one of the distal end of the proximal core section and the proximal end of the distal core section includes a taper.

7. The guide wire of claim 1, wherein at least one of the distal end of the proximal core section and the proximal end of the distal core section has a reduced diameter.

8. The guide wire of claim 1, wherein the flexible sleeve is a polymeric sleeve.

9. The guide wire of claim 8, wherein the polymeric sleeve is a polyimide sleeve.

10. The guide wire of claim 8, wherein the polymeric sleeve has an outer diameter generally equal to the outer diameter of the core.

11. The guide wire of claim 8, further comprising a mass of hardened material connecting the distal end of the proximal core section to the proximal end of the distal core section inside the polymeric sleeve.

12. A method for joining two intravascular guide wire core materials, comprising:
    providing a proximal core section with a proximal and distal end and a distal core section with a proximal and distal end;
    forming a complementary shape into the distal end of the proximal core section and the proximal end of the distal core section;
    providing a flexible sleeve having proximal and distal ends;
    creating a plurality of openings in the sleeve so that each end of the sleeve has a plurality of circumferential discontinuities; and
    inserting the proximal and distal core sections into the flexible sleeve in opposing directions with the complementary shaped ends overlapping one another.

13. The method of claim 12, wherein forming the complementary shape, the complementary shape includes a taper.

14. The method of claim 13, further comprising filling the flexible sleeve with a mass of material before inserting the proximal and distal core sections into the flexible sleeve, wherein the mass of material joins the proximal and distal core sections together.

15. The method of claim 14, wherein filling the flexible sleeve with a mass of material, the flexible sleeve is a polymeric sleeve.

16. The method of claim 15, wherein the polymeric sleeve is a polyimide sleeve.

17. The method of claim 12, further comprising disposing serration on the complementary shaped ends.

18. The method of claim 12, further comprising reducing the outer diameter of at least one of the distal end of the proximal core section and the proximal end of the distal core section prior to forming the complementary shaped ends.

19. The method of claim 12, further comprising reducing the outer diameter of at least one of the distal end of the proximal core section and the proximal end of the distal core section after forming the complementary shaped ends.

* * * * *

UNITED STATES PATENT AND TRADEMARK OFFICE
CERTIFICATE OF CORRECTION

PATENT NO. : 6,866,642 B2
DATED : March 15, 2005
INVENTOR(S) : Brad Kellerman et al.

It is certified that error appears in the above-identified patent and that said Letters Patent is hereby corrected as shown below:

Column 2,
Line 43, delete "embodiments" and insert -- embodiment --.

Column 4,
Line 8, delete "grind" and insert -- ground --.
Line 60, delete "is that is" and insert -- is that it --.
Line 63, delete "is that" and insert -- is that it --.

Column 6,
Line 30, delete "is that is" and insert -- is that it --.

Column 9,
Line 3, delete "claim 13" and insert -- claim 12 --.

Signed and Sealed this

Second Day of August, 2005

JON W. DUDAS
*Director of the United States Patent and Trademark Office*